(12) United States Patent
Seto et al.

(10) Patent No.: US 7,306,164 B2
(45) Date of Patent: Dec. 11, 2007

(54) BIOCHEMICAL ANALYSIS METHOD AND APPARATUS

(75) Inventors: Yoshihiro Seto, Minamiashigara (JP); Nobuaki Tokiwa, Minamiashigara (JP); Yoichi Endo, Minamiashigara (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 11/588,292

(22) Filed: Oct. 27, 2006

(65) Prior Publication Data

US 2007/0041868 A1 Feb. 22, 2007

Related U.S. Application Data

(62) Division of application No. 10/397,262, filed on Mar. 27, 2003.

(30) Foreign Application Priority Data

Mar. 27, 2002 (JP) ............... 2002-089030
Mar. 28, 2002 (JP) ............... 2002-092286

(51) Int. Cl.
*G06K 19/06* (2006.01)
*G01N 31/22* (2006.01)

(52) U.S. Cl. ............... 235/494; 422/56; 422/58; 235/462.02; 235/462.04; 235/487; 436/46

(58) Field of Classification Search ............... 422/56
See application file for complete search history.

(56) References Cited

U.S. PATENT DOCUMENTS 4,476,149 A * 10/1984 Poppe et al. ............... 427/2.13
5,902,982 A * 5/1999 Lappe ............... 235/375
5,945,341 A * 8/1999 Howard, III ............... 436/46
6,284,550 B1 * 9/2001 Carroll et al. ............... 436/514

FOREIGN PATENT DOCUMENTS

| JP | 60-12553 A | 7/1985 |
| JP | 7-315558 A | 12/1995 |
| JP | 2001-349834 A | 12/2001 |
| JP | 2001-349835 A | 12/2001 |
| WO | WO 01/11533 A1 | 2/2001 |

* cited by examiner

*Primary Examiner*—Jill Warden
*Assistant Examiner*—Neil Turk
(74) *Attorney, Agent, or Firm*—Sughrue Mion, Pllc.

(57) ABSTRACT

Samples and dry chemical analysis elements, which are necessary for analyses of the samples, are loaded on a sample tray. Each sample is sucked with a spotting nozzle of a spotting unit and spotted onto one dry chemical analysis element. Analysis information, which contains information representing a type of analysis, is appended to each dry chemical analysis element. The analysis information is read with a reading device located such that, when a certain sample is located at a position for sample suction by an operation of the sample tray, the reading device reads the analysis information, which has been appended to a next dry chemical analysis element to be used for the analysis of the certain sample, at a position at which the next dry chemical analysis element is located.

3 Claims, 6 Drawing Sheets

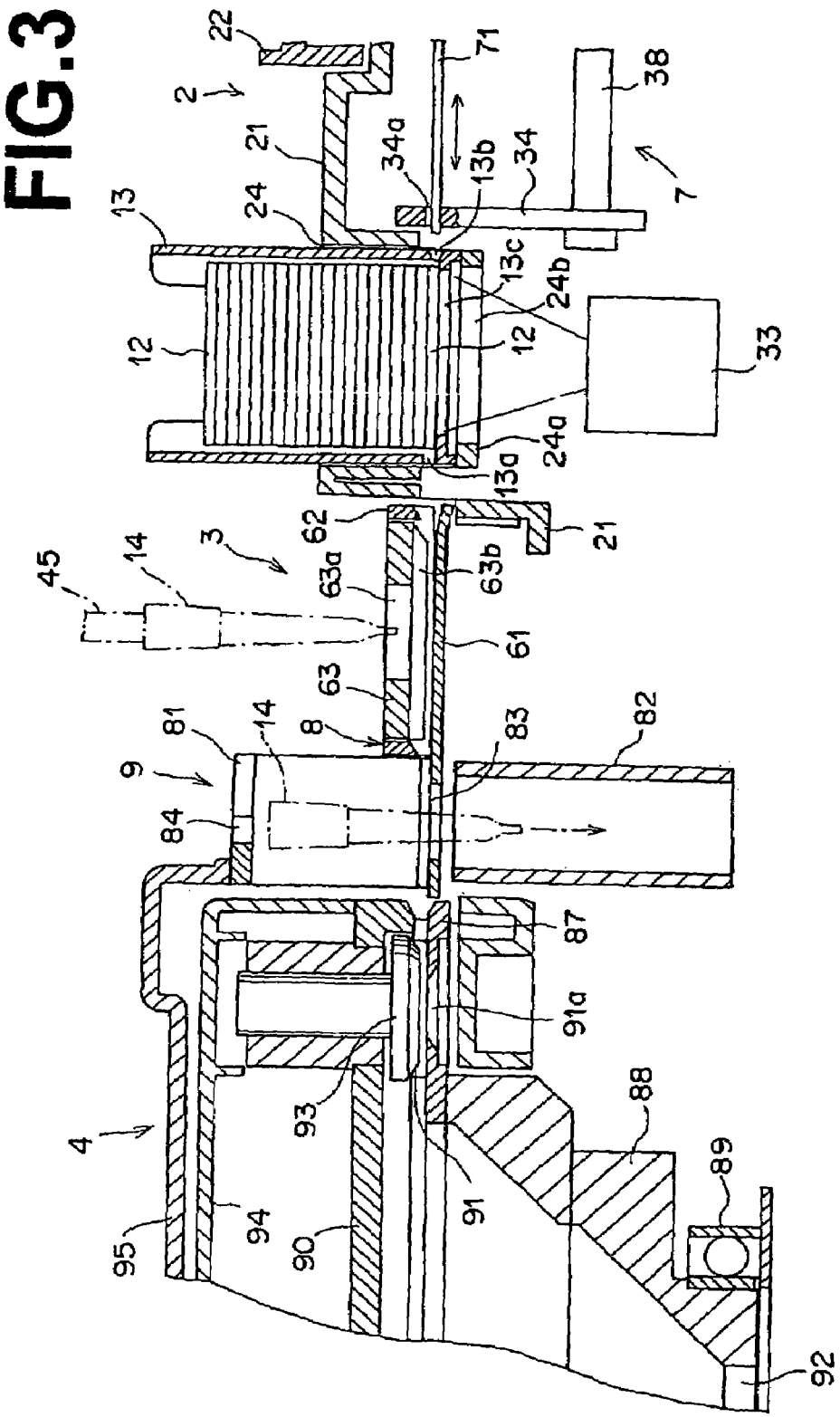

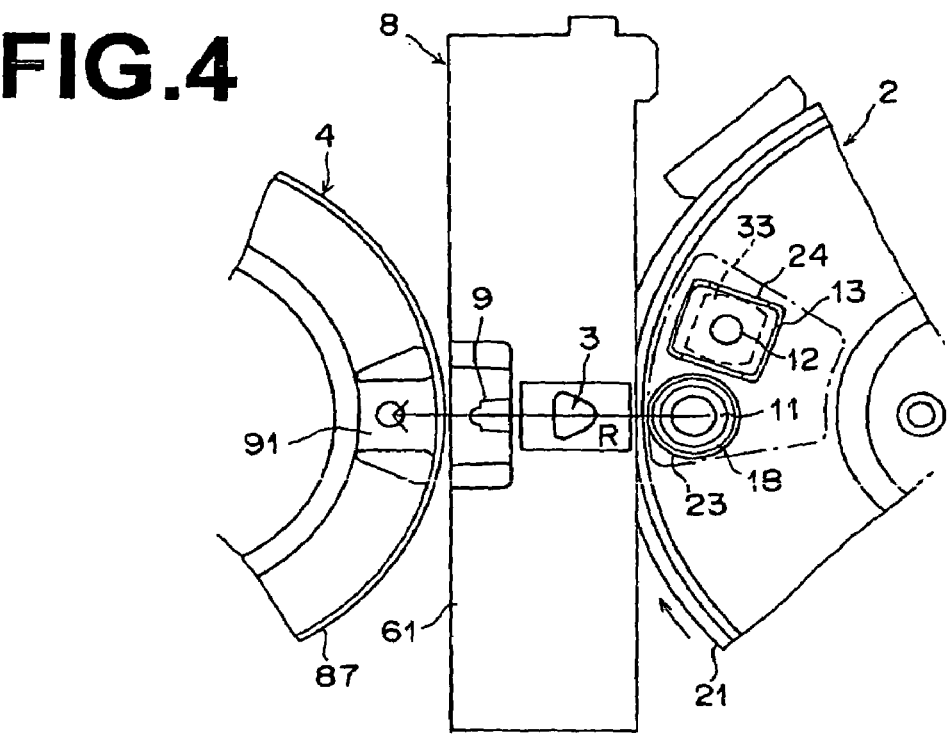
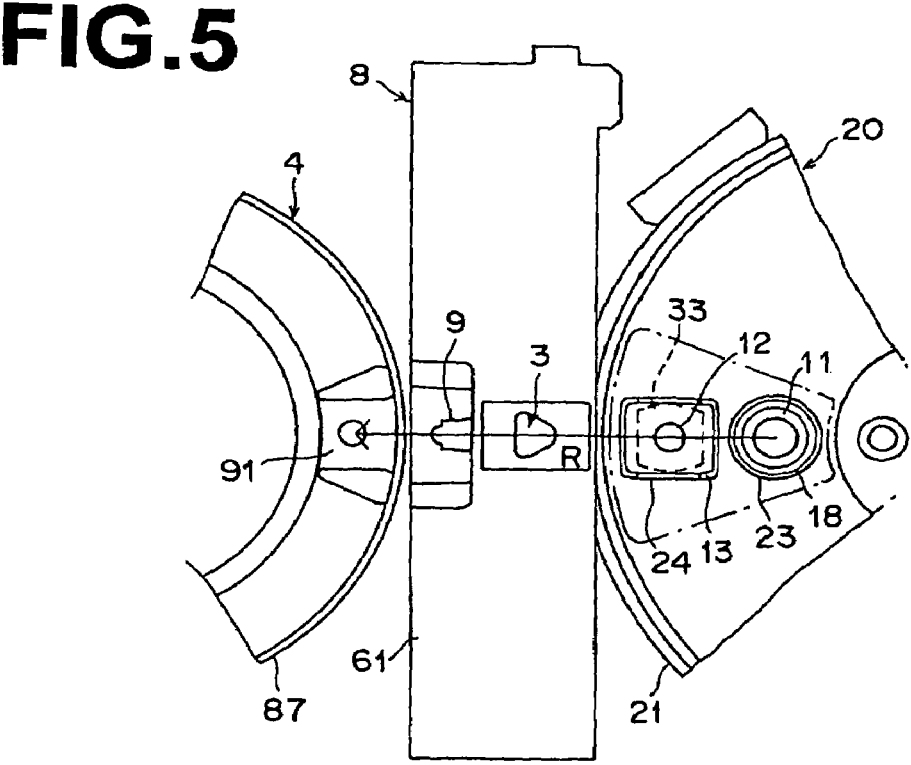

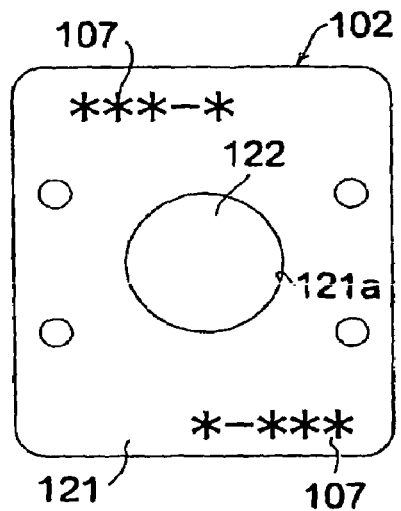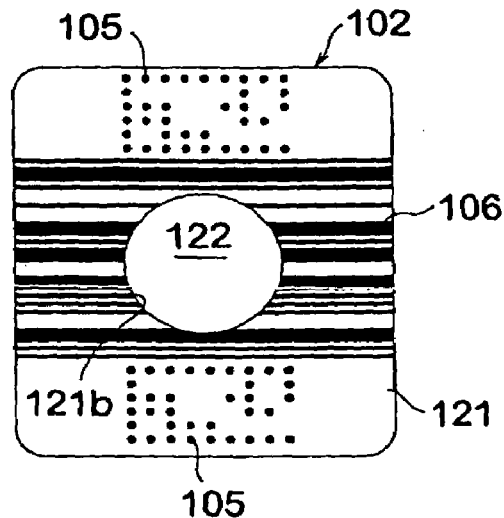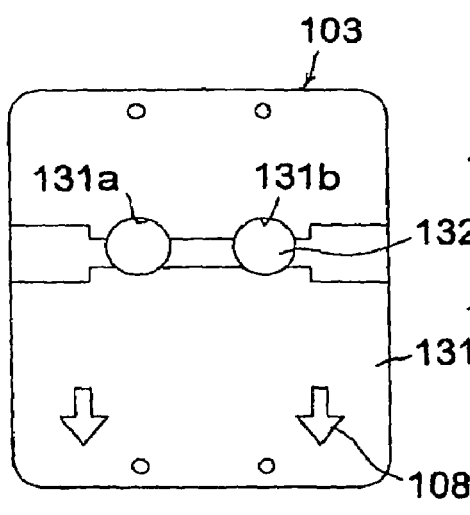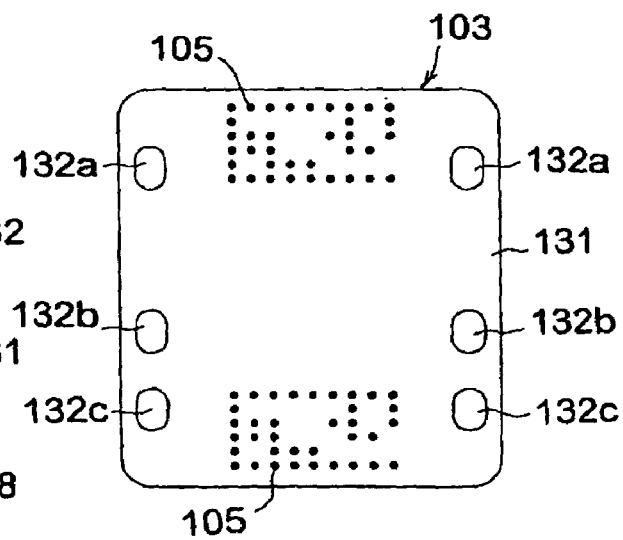

BIOCHEMICAL ANALYSIS METHOD AND APPARATUS

This is a divisional of application Ser. No. 10/397,262 filed Mar. 27, 2003. The entire disclosure of the prior application, application Ser. No. 10/397,262, is considered part of the disclosure of the accompanying divisional application and is hereby incorporated by reference.

BACKGROUND OF THE INVENTION

1. Field of the Invention

This invention relates to a biochemical analysis method and apparatus, wherein a sample, such as blood or urine, is spotted onto a dry chemical analysis element, such as a colorimetric-type dry chemical analysis element or an electrolyte-type dry chemical analysis element, by use of a spotting unit, and a substance concentration of a specific biochemical substance contained in the sample, an ionic activity of a specific ion contained in the sample, or the like, is determined. This invention also relates to a dry chemical analysis element for biochemical analysis and particularly to a technique for imparting analysis information, and the like, to the dry chemical analysis element.

2. Description of the Related Art

Colorimetric-type dry chemical analysis elements and electrolyte-type dry chemical analysis elements have heretofore been used in practice. When a droplet of a sample is merely spotted onto the colorimetric-type dry chemical analysis element, a specific chemical constituent or a specific physical constituent contained the sample is capable of being analyzed quantitatively. Also, when a droplet of a sample is merely spotted on to the electrolyte-type dry chemical analysis element, an ionic activity of a specific ion contained the sample is capable of being analyzed quantitatively. Biochemical analysis apparatuses utilizing the dry chemical analysis elements are capable of performing sample analyses easily and quickly and have therefore been utilized widely in medical facilities, medical laboratories, and the like.

Colorimetry utilizing colorimetric-type dry chemical analysis elements is performed in the manner described below. Specifically, after a sample has been spotted onto a dry chemical analysis element, the dry chemical analysis element having been spotted with the sample is kept at a constant temperature for a predetermined time within an incubator and is thereby caused to undergo a color reaction (i.e., a dye forming reaction). Thereafter, measuring light, which has wavelengths selected previously in accordance with a combination of a predetermined biochemical substance contained in the sample and a reagent contained in the dry chemical analysis element, is irradiated to the dry chemical analysis element, and an optical density of the dry chemical analysis element is thereby measured. The concentration of the predetermined biochemical substance contained in the sample is determined from the measured optical density and by use of a calibration curve having been formed previously, which represents a correspondence relationship between the optical density and the substance concentration of the predetermined biochemical substance.

Potentiometry utilizing electrolyte-type dry chemical analysis elements is performed in the manner described below. Specifically, in lieu of the optical density described above being measured, the ionic activity of a specific ion contained in a sample, which has been spotted onto an electrode pair comprising a pair of two dry type ion selective electrodes of an identical type, is determined through quantitative analysis with potentiometry by use of a reference liquid.

In each of the colorimetry and the potentiometry described above, the liquid-state sample is accommodated in a sample vessel (such as a blood-collecting tube), and the sample vessel accommodating the sample is set on a biochemical analysis apparatus. Also, the dry chemical analysis element necessary for the measurement is loaded into the biochemical analysis apparatus. Further, the dry chemical analysis element is conveyed from a position for element loading into a spotting section and into an incubator. Furthermore, the sample is fed by a spotting nozzle from a position for sample loading to the spotting section and spotted onto the dry chemical analysis element.

The kind of the dry chemical analysis element and the technique for the sample spotting onto the dry chemical analysis element vary in accordance with the type of the analysis. Therefore, each of the dry chemical analysis elements utilized for the analyses is appended with analysis information, which contains information representing the type of the analysis, by use of a bar code recording technique, or the like. Also, in cases where the dry chemical analysis element is loaded onto a sample tray of a biochemical analysis apparatus directly or by use of a cartridge, the biochemical analysis apparatus is controlled such that the dry chemical analysis element is taken out from the sample tray, the analysis information is read from the dry chemical analysis element, and an operation for sucking a sample, which corresponds to the type of the analysis to be made with the dry chemical analysis element, is performed in accordance with the analysis information having been read from the dry chemical analysis element.

Also, ordinarily, a plurality of types of analyses are performed with respect to one sample. Therefore, there have heretofore been proposed biochemical analysis apparatuses, in which a plurality of kinds of dry chemical analysis elements are loaded in a laid-up state on a sample tray in accordance with each sample, and analyses are performed successively by use of the dry chemical analysis elements. In such cases, in order for the one sample to be successively spotted onto the plurality of the kinds of the dry chemical analysis elements, it is necessary that the operation for reading the analysis information and the operation for sucking the sample are iterated with respect to each of the dry chemical analysis elements.

Ordinarily, the operation for reading the analysis information, which has been appended to the dry chemical analysis element, from the dry chemical analysis element is performed in the manner described below. Specifically, information reading means is located at an intermediate point of an element conveyance path, along which the dry chemical analysis element having been taken out from the sample tray, is conveyed to the position for sample spotting. Also, the operation for reading the analysis information is performed in accordance with the operation for conveying the dry chemical analysis element.

However, with the aforesaid technique for reading the analysis information from the dry chemical analysis element, if the dry chemical analysis element having been taken out from the sample tray onto the element conveyance path is conveyed in a state in which the front surface and the back surface of the dry chemical analysis element are reversed or in a state in which the orientation of the dry chemical analysis element is incorrect, the problems will occur in that the analysis cannot be made accurately, and the analysis information cannot be read from the dry chemical analysis element. In such cases, warning, or the like, is given by the reading means. However, in such cases, the dry chemical analysis element, which has already been sent onto the element conveyance path must be taken out from the element conveyance path, the conveyance of the dry chemical analysis element must then performed again, and the operation for reading the analysis information from the dry chemical analysis element must again be performed. Therefore, a considerable time and labor are required, and the processing efficiency cannot be kept high. Also, in cases where, for example, the biochemical analysis apparatus comes short of expendables, or the sample and the dry chemical analysis element do not conform to each other, after the analysis operation has been started, a necessary correcting operation must be performed, and the analysis operation must then be performed again. In such cases, a considerable time and labor are required.

In order for the problems described above to be solved, it may be considered that the operation for reading the analysis information from the dry chemical analysis element is performed in the state, in which the dry chemical analysis element is loaded on the sample tray, and before the conveyance of the dry chemical analysis element is started. However, in such cases, it becomes necessary, depending upon the position at which the reading means is located, that the sample tray is moved to the position for information reading, then moved to the position for element takeout, and thereafter moved to the position for sample suction. Therefore, the problems occur in that control of the operation of the sample tray and sequence control cannot be kept simple, a considerable time is required to perform the processing, and the analyses cannot be performed quickly.

SUMMARY OF THE INVENTION

The primary object of the present invention is to provide a biochemical analysis method, wherein an operation for reading analysis information, which has been appended to a dry chemical analysis element, from the dry chemical analysis element and an operation for sucking a sample are capable of being performed efficiently.

Another object of the present invention is to provide a biochemical analysis apparatus for carrying out the biochemical analysis method.

A further object of the present invention is to provide a dry chemical analysis element for biochemical analysis, on which information is capable of being recorded such that information representing a production lot of the dry chemical analysis element and analysis management information are capable of being matched with each other.

The present invention provides a biochemical analysis method, comprising the steps of:

i) loading a plurality of samples and a plurality of dry chemical analysis elements, which are necessary for analyses of the samples, on a sample tray, ii) sucking each of the samples, which have been loaded on the sample tray, with a spotting nozzle of a spotting unit, and iii) spotting the sucked sample onto one of the dry chemical analysis elements with the spotting nozzle of the spotting unit, wherein analysis information, which contains information representing a type of analysis, is appended to each of the dry chemical analysis elements, and the analysis information having been appended to each of the dry chemical analysis elements is read with reading means located such that, at the time at which a certain sample is located at a position for sample suction by an operation of the sample tray, the reading means is capable of reading the analysis information, which has been appended to a next dry chemical analysis element to be used for the analysis of the certain sample, from the next dry chemical analysis element and at a position at which the next dry chemical analysis element is located.

The present invention also provides a biochemical analysis apparatus, comprising:

i) a sample tray, which is capable of being loaded with a plurality of samples and a plurality of dry chemical analysis elements necessary for analyses of the samples, and ii) a spotting unit for sucking each of the samples, which have been loaded on the sample tray, with a spotting nozzle and spotting the sucked sample onto one of the dry chemical analysis elements with the spotting nozzle, wherein analysis information, which contains information representing a type of analysis, is appended to each of the dry chemical analysis elements, and reading means for reading the analysis information having been appended to each of the dry chemical analysis elements is located such that, at the time at which a certain sample is located at a position for sample suction by an operation of the sample tray, the reading means is capable of reading the analysis information, which has been appended to a next dry chemical analysis element to be used for the analysis of the certain sample, from the next dry chemical analysis element and at a position at which the next dry chemical analysis element is located.

The biochemical analysis apparatus in accordance with the present invention should preferably be modified such that a number of dry chemical analysis elements, which number corresponds to the types of the analyses to be made with respect to one sample, are loaded in a laid-up state on the sample tray, the laid-up dry chemical analysis elements are conveyed to a position for sample spotting one after another in an ascending order, beginning with the lowest dry chemical analysis element, and successively spotted with the sample at the position for sample spotting, and the reading means reads the analysis information, which has been appended to a bottom surface of a dry chemical analysis element to be conveyed next.

Also, the biochemical analysis apparatus in accordance with the present invention should preferably be modified such that the dry chemical analysis elements are accommodated in an element cartridge, and the element cartridge, in which the dry chemical analysis elements have been accommodated, is loaded on the sample tray.

Further, the biochemical analysis apparatus in accordance with the present invention should preferably be modified such that the dry chemical analysis elements are accommodated in an element cartridge, the element cartridge, in which the dry chemical analysis elements have been accommodated, is loaded on the sample tray, and a window for information reading is formed at a bottom of the element cartridge.

Furthermore, the biochemical analysis apparatus in accordance with the present invention should preferably be modified such that each of the samples and the dry chemical analysis elements necessary for analyses of the sample are located on the sample tray such that the sample and the dry chemical analysis elements form a pair with each other.

Also, the biochemical analysis apparatus in accordance with the present invention should preferably be modified such that the reading means is located at a position under the sample tray.

Further, the biochemical analysis apparatus in accordance with the present invention should preferably be modified such that the sample tray has a circular shape and is moved to a position for element takeout and the position for sample suction through a rotating operation.

Alternatively, the movement of the sample tray may be performed through a linear movement operation.

The present invention further provides a dry chemical analysis element for biochemical analysis, comprising:

i) a mount section, and ii) an analyzing region, which is to be spotted with a sample, the analyzing region being supported on the mount section, wherein analysis type information (such as information representing an analysis type number and information representing a sample kind number), production lot information (such as information representing a production lot and information representing an inherent number concerning the production), and advance direction information have been recorded on a surface of the mount section and with a dot recording technique for recording information by a dot array pattern.

The dry chemical analysis element for biochemical analysis in accordance with the present invention should preferably be modified such that the advance direction information is recorded by the absence of notation at a dot located at a specific site in the dot array pattern.

Also, the dry chemical analysis element for biochemical analysis in accordance with the present invention should preferably be modified such that the dot array pattern is recorded at a position other than positions which overlap upon a bar code recording region having already been formed on the mount section, and both the dot array pattern and a bar code are capable of being recorded on the dry chemical analysis element.

Further, the dry chemical analysis element for biochemical analysis in accordance with the present invention should preferably be modified such that the dot array pattern is recorded by use of a plurality of colors. In such cases, the amount of information recorded is capable of being kept large. Furthermore, information representing a serviceable life should preferably be recorded.

The biochemical analysis apparatus for performing an analysis by use of the dry chemical analysis element for biochemical analysis in accordance with the present invention is provided with means for reading the dot array pattern from the dry chemical analysis element and a control unit for matching the analysis type information and the production lot information, which have been read from the dry chemical analysis element, and analysis management information, which corresponds to the dry chemical analysis element and has been read with a different reading operation, with each other. The control unit should preferably be constituted so as to store a plurality of pieces of analysis management information.

With the biochemical analysis method and apparatus in accordance with the present invention, the analysis information, which contains the information representing the type of the analysis, is appended to each of the dry chemical analysis elements. Also, the analysis information having been appended to each of the dry chemical analysis elements is read with the reading means located such that, at the time at which a certain sample is located at the position for sample suction by the operation of the sample tray, the reading means is capable of reading the analysis information, which has been appended to the next dry chemical analysis element to be used for the analysis of the certain sample, from the next dry chemical analysis element and at the position at which the next dry chemical analysis element is located. Therefore, at the time at which the operation for sucking the sample to be spotted to a dry chemical analysis element located at the position for sample spotting is performed, the operation for reading the analysis information from the next dry chemical analysis element is capable of being performed simultaneously by the reading means. Accordingly, movement of the sample tray for the information reading becomes unnecessary, and sequence control is capable of being simplified. As a result, a plurality of types of analyses are capable of being made efficiently.

With the biochemical analysis apparatus, wherein the reading means is located under the sample tray, the analysis information is capable of being read before the conveyance of the dry chemical analysis element toward the position for sample spotting is performed. Therefore, in cases where a failure is found from the information having been read, a warning is capable of being given. Also, since the analysis operation has not yet been started substantially at this time, correcting operations with respect to shortage of expendables, inconformity of the sample and the type of the analysis with each other, and the like, are capable of being performed easily.

Also, with the biochemical analysis apparatus in accordance with the present invention, in cases where a plurality of sets of the samples and the dry chemical analysis elements are loaded on the sample tray, the operation for reading the information from the dry chemical analysis element, the operation for takeout and conveyance of the dry chemical analysis element, and the operation for sucking and spotting the sample are capable of being performed successively and efficiently. Therefore, as a whole, the unit analyzing time is capable of being kept short.

With the dry chemical analysis element for biochemical analysis in accordance with the present invention, the analysis type information, the production lot information, and the advance direction information have been recorded on the surface of the mount section and with the dot recording technique for recording information by the dot array pattern. Therefore, the analysis type information and the production lot information, which have been recorded on the dry chemical analysis element, and the analysis management information are capable of being matched with each other. Accordingly, the biochemical analysis is capable of being performed accurately in accordance with the accurate analysis management information, and the reliability of the biochemical analysis is capable of being enhanced.

Also, with the dry chemical analysis element for biochemical analysis in accordance with the present invention, erroneous setting of an electrolyte-type dry chemical analysis element with respect to the advance direction of the dry chemical analysis element is capable of being detected, and a warning is capable of being given.

With the dry chemical analysis element for biochemical analysis in accordance with the present invention, the dot array pattern may be recorded at the position other than the positions which overlap upon the bar code recording region having already been formed on the mount section, such that both the dot array pattern and the bar code are capable of being recorded on the dry chemical analysis element. In such cases, the dry chemical analysis element for biochemical analysis in accordance with the present invention is capable of being utilized in a conventional biochemical analysis apparatus.

In cases where a plurality of pieces of the analysis management information are stored in the control unit of the biochemical analysis apparatus, the dry chemical analysis elements corresponding to different pieces of analysis management information are capable of being loaded in a mixed state to the biochemical analysis apparatus. Therefore, in cases where a sample is to be analyzed urgently, the analysis processing need not be ceased and is capable of being performed efficiently.

BRIEF DESCRIPTION OF THE DRAWINGS

FIG. 3 is a sectional front view showing sections along an element conveyance path for dry chemical analysis elements, FIG. 4 is a schematic plan view showing a state in which a sample tray has been moved to a position for information reading, FIG. 5 is a schematic plan view showing a major part of a different embodiment of the biochemical analysis apparatus in accordance with the present invention, FIG. 6A is a plan view showing an embodiment of the dry chemical analysis element for biochemical analysis in accordance with the present invention, which is constituted as a colorimetric-type dry chemical analysis element, FIG. 6B is a bottom view showing the embodiment of the dry chemical analysis element shown in FIG. 6A, FIG. 7A is a plan view showing a different embodiment of the dry chemical analysis element for biochemical analysis in accordance with the present invention, which is constituted as an electrolyte-type dry chemical analysis element, FIG. 7B is a bottom view showing the embodiment of the dry chemical analysis element shown in FIG. 7A.

DESCRIPTION OF THE PREFERRED EMBODIMENTS

The present invention will hereinbelow be described in further detail with reference to the accompanying drawings.

Figure 1:
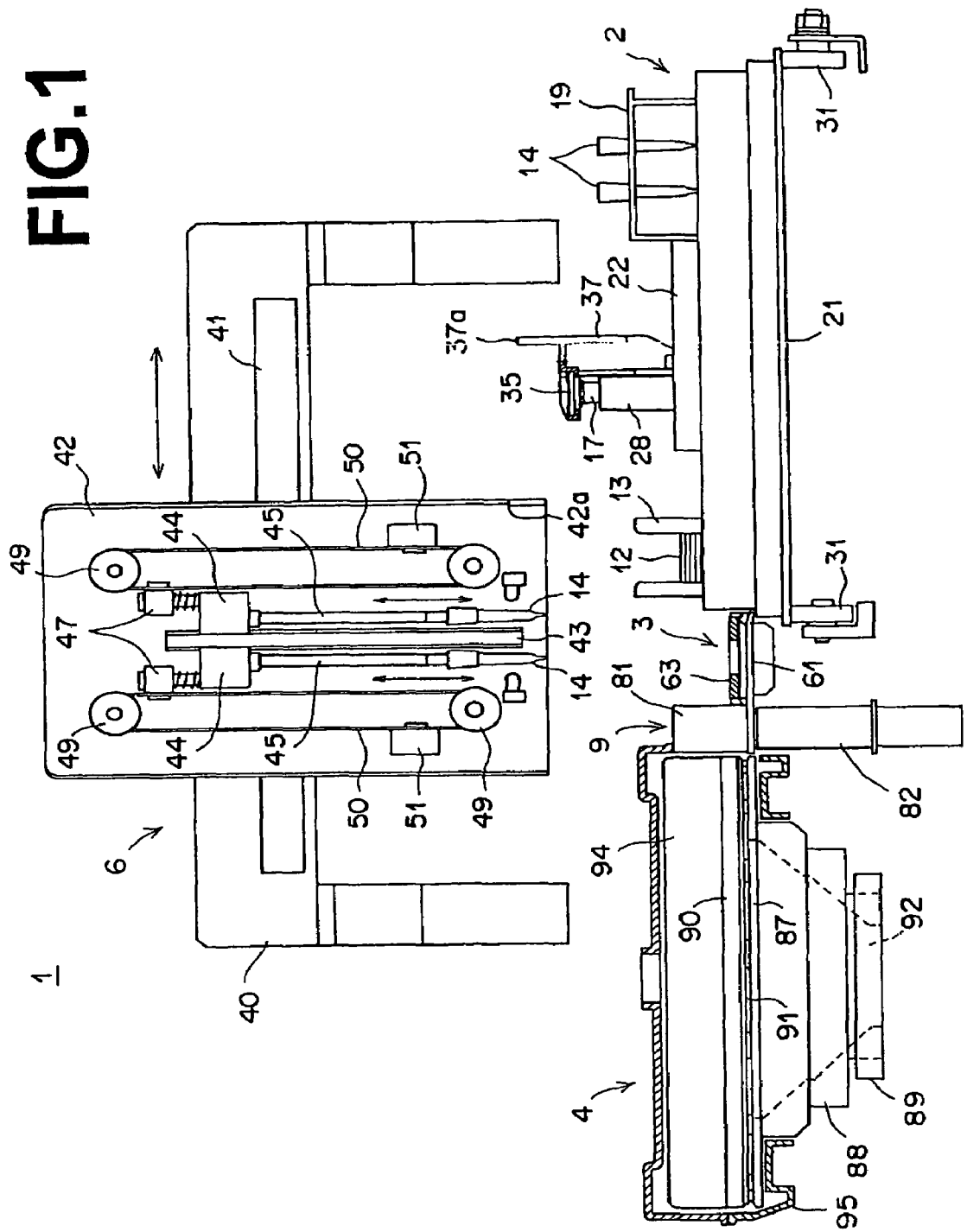
FIG. 1 is a partially sectional front view showing an embodiment of the biochemical analysis apparatus in accordance with the present invention.
Figure 2:
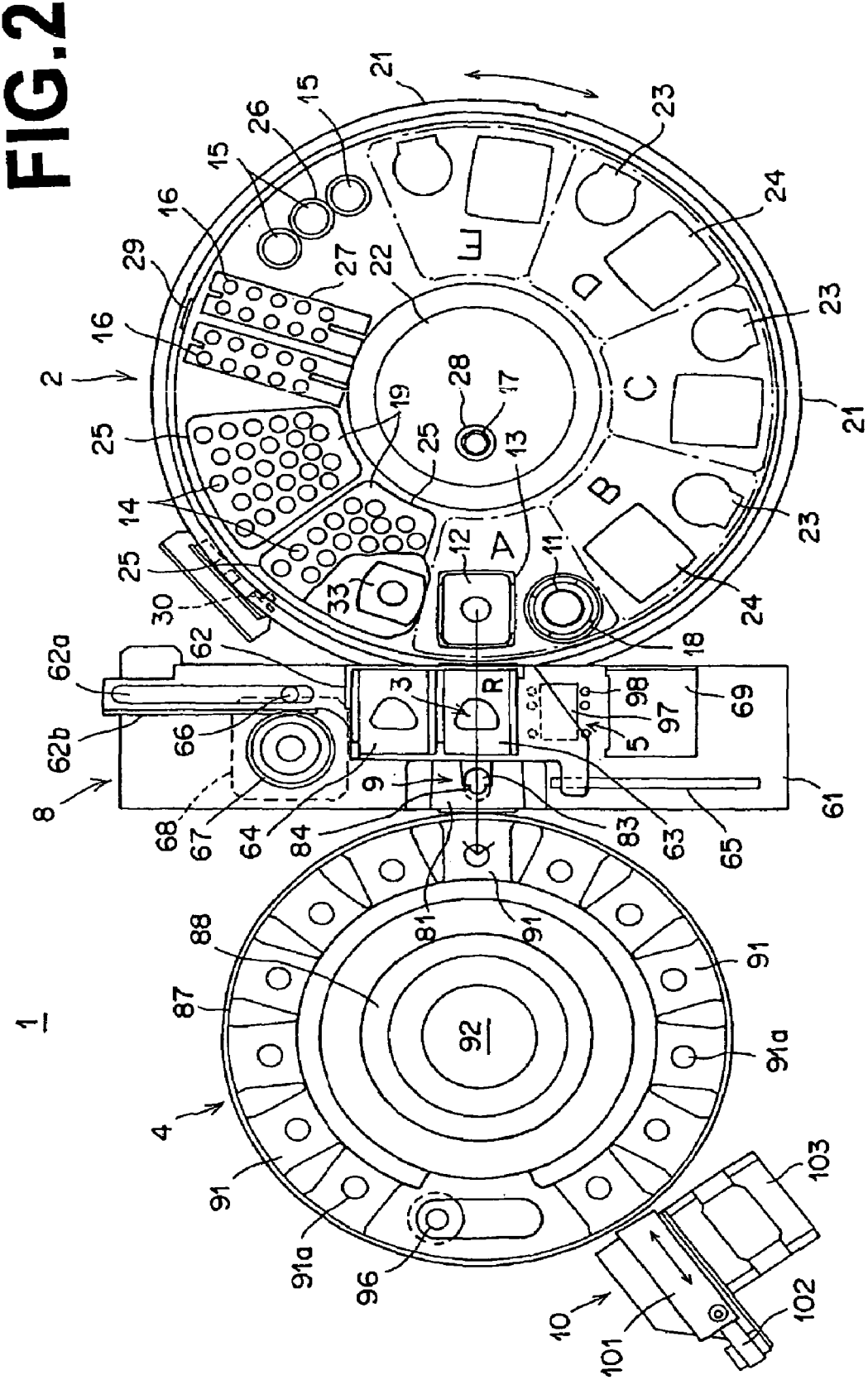
FIG. 2 is a plan view showing a major part of the embodiment of FIG. 1 with a spotting unit being omitted for clearness.

FIG. 1 is a partially sectional front view showing an embodiment of the biochemical analysis apparatus in accordance with the present invention. FIG. 2 is a plan view showing a major part of the embodiment of FIG. 1 with a spotting unit being omitted for clearness. FIG. 3 is a sectional front view showing sections along an element conveyance path for dry chemical analysis elements. FIG. 4 is a schematic plan view showing a state in which a sample tray has been moved to a position for information reading.

A biochemical analysis apparatus 1 comprises a sample tray 2, a spotting section 3, a first incubator 4, a second incubator 5, a spotting unit 6, an element conveying mechanism 7, a transfer mechanism 8, a tip scrapping section 9, and an element scrapping mechanism 10.

The sample tray 2 has a circular shape and is loaded with a plurality of sample vessels 11, 11, . . . , each of which accommodates one of samples, a plurality of element cartridges 13, 13, . . . , each of which accommodates a plurality of dry chemical analysis elements 12, 12, . . . (colorimetric-type dry chemical analysis elements and/or electrolyte-type dry chemical analysis elements) having not been used, and expendables (nozzle tips 14, 14, . . . , diluent liquid vessels 15, 15, 15, mixing cups 16, 16, . . . , and a reference liquid vessel 17). Each of the sample vessels 11, 11, . . . is loaded via a sample adapter 18 on the sample tray 2. The nozzle tips 14, 14, . . . are accommodated in each of tip racks 19, 19 and are loaded in this form on the sample tray 2.

The spotting section 3 is located on an extension of a center line of the sample tray 2. In the spotting section 3, a sample, such as blood plasma, whole blood, blood serum, or urine, is spotted to the dry chemical analysis element 12 having been conveyed into the spotting section 3. Specifically, with the spotting unit 6, the sample is spotted onto the colorimetric-type dry chemical analysis element 12. Also, the sample and a reference liquid are spotted onto the electrolyte-type dry chemical analysis element 12. The tip scrapping section 9 for scrapping each of the nozzle tips 14, 14, . . . is located on the side downstream from the spotting section 3.

The first incubator 4 has a circular shape and is located at a position on an extension of the tip scrapping section 9. The first incubator 4 accommodates the dry chemical analysis elements 12, 12, . . . , which are of the colorimetric types, and keeps the temperature of the colorimetric-type dry chemical analysis elements 12, 12, . . . at a constant temperature for a predetermined length of time in order to perform colorimetry. As illustrated in FIG. 2, the second incubator 5 is located at a position in the vicinity of a side of the spotting section 3. The second incubator 5 accommodates the dry chemical analysis element 12, which is of the electrolyte type. Also, the second incubator 5 keeps the temperature of the electrolyte-type dry chemical analysis element 12 at a constant temperature for a predetermined length of time in order to perform potentiometry.

As illustrated in FIG. 3, the element conveying mechanism 7 is provided with an element conveying member (a conveying bar) 71. Though not shown in detail, the element conveying member 71 is located within the sample tray 2. The element conveying mechanism 7 conveys the dry chemical analysis elements 12, 12, . . . one after another from the sample tray 2 into the spotting section 3 and then into the first incubator 4 along a straight element conveyance path R (illustrated in FIG. 2). As illustrated in FIG. 2, the element conveyance path R connects a center point of the sample tray 2 and a center point of the first incubator 4 with each other and passes through the spotting section 3 and the tip scrapping section 9. The element conveying member 71 is supported for sliding movement by a guide rod 38 and is operated for reciprocal movement by a driving mechanism (not shown). The leading end of the element conveying member 71 is inserted through a guide hole 34a of a vertical plate 34. The element conveying member 71 slides in the guide hole 34a.

The transfer mechanism 8 is formed so as to act also as the spotting section 3. The transfer mechanism 8 transfers the electrolyte-type dry chemical analysis element 12 from the spotting section 3 into the second incubator 5 along a direction normal to the element conveyance path R.

The spotting unit 6 is located at an upper part of the biochemical analysis apparatus 1. The spotting unit 6 is provided with spotting nozzles 45, 45 which are capable of being moved vertically. The spotting nozzles 45, 45 move on the straight line identical with the element conveyance path R described above in order to perform the spotting of the samples and the reference liquid, and dilution of the samples with a diluent liquid. The nozzle tip 14 is fitted to a bottom end of each of the spotting nozzles 45, 45. Each of the spotting nozzles 45, 45 sucks the sample, the reference liquid, or the like, into the nozzle tip 14 and discharges the sucked liquid from the nozzle tip 14. The spotting unit 6 is provided with syringe means (not shown) for performing the suction and the discharging of the liquid. In the tip scrapping section 9, the nozzle tip 14, which has been used, is removed from each of the spotting nozzles 45, 45, allowed to fall, and thus scrapped.

The element scrapping mechanism 10 is associated with the first incubator 4. The element scrapping mechanism 10 pushes the colorimetric-type dry chemical analysis element 12, which has been used for the analysis, toward a center region of the first incubator 4. At the center region of the first incubator 4, the colorimetric-type dry chemical analysis element 12 is allowed to fall and is thus scrapped. The colorimetric-type dry chemical analysis element 12 is also capable of being scrapped by the element conveying mechanism 7 described above. The electrolyte-type dry chemical analysis element 12, which has been used for the analysis at the second incubator 5, is scrapped by the transfer mechanism 8 described above into a scrapping hole 69.

Though not shown, a blood filtering unit for separating blood plasma from blood is located in the vicinity of the sample tray 2.

The biochemical analysis apparatus 1 will hereinbelow be described in more detail. The sample tray 2 comprises a circular rotating disk 21, which is capable of being rotated forwardly and reversely, and a circular disk-shaped non-rotating section 22, which is formed at the center region of the sample tray 2.

As illustrated in FIG. 2, the rotating disk 21 is provided with five sample loading sections 23, 23, . . . (indicated by A, B, C, D, and E). Each of the sample loading sections 23, 23, . . . supports the sample vessel 11, such as a blood-collecting tube accommodating the sample, via the sample adapter 18. The rotating disk 21 is also provided with five element loading sections 24, 24, . . . , each of which is located in the vicinity of one of the sample loading sections 23, 23, . . . . Each of the element loading sections 24, 24, . . . supports the element cartridge 13, in which the plurality of the dry chemical analysis elements 12, 12, . . . having not been used are accommodated in the laid-up state. Ordinarily, multiple kinds of dry chemical analysis elements 12, 12, . . . are prepared in accordance with the types of analyses of the samples. The rotating disk 21 is further provided with two tip loading sections 25, 25. Each of the tip loading sections 25, 25 supports a tip rack 19 having a plurality of support holes arrayed for accommodating the plurality of the nozzle tips 14, 14, . . . . The rotating disk 21 is still further provided with a diluent liquid loading section 26 for supporting the three diluent liquid vessels 15, 15, 15, which accommodate the diluent liquid. The rotating disk 21 is also provided with a cup loading section 27 for supporting a plurality of the mixing cups 16, 16, . . . , in each of which the diluent liquid and the sample are to be mixed with each other. (The mixing cups 16, 16, . . . are formed as cup-shaped recesses located on a molded product.) The sample loading sections 23, 23, . . . , the element loading sections 24, 24, . . . , the tip loading sections 25, 25, the diluent liquid loading section 26, and the cup loading section 27 are located around the center region of the rotating disk 21.

The non-rotating section 22 is provided with a cylindrical reference liquid loading section 28 for supporting the reference liquid vessel 17, which accommodates the reference liquid. The reference liquid loading section 28 is located on the extension of the element conveyance path R and within the movement range of the spotting nozzles 45, 45. As illustrated in FIG. 1, an evaporation preventing cover 35, which opens and closes the opening of the reference liquid vessel 17, is located at the reference liquid loading section 28.

The evaporation preventing cover 35 is supported by a swinging member 37, whose bottom end is pivotably supported on the non-rotating section 22. The evaporation preventing cover 35 is urged toward the direction which closes the opening of the reference liquid vessel 17. The swinging member 37 has an engagement region 37a, which is projected at the top end region of the swinging member 37. The engagement region 37a of the swinging member 37 is capable of being brought into abutment with a bottom end corner region 42a of a moving frame 42 of the spotting unit 6. Also, when the moving frame 42 of the spotting unit 6 is moved to the position above the reference liquid loading section 28 in order to perform the suction of the reference liquid with one of the spotting nozzles 45, 45, the bottom end corner region 42a of the moving frame 42 comes into abutment with the engagement region 37a of the evaporation preventing cover 35. As a result, the swinging member 37 is swung to the opening position. Also, the evaporation preventing cover 35 opens the reference liquid vessel 17. Therefore, it becomes possible for the spotting nozzle 45 to suck the reference liquid accommodated in the reference liquid vessel 17. When the moving frame 42 is moved toward the spotting section 3, the evaporation preventing cover 35 closes the opening of the reference liquid vessel 17. In this state, the reference liquid is prevented from evaporating. Therefore, the problems are capable of being prevented from occurring in that the accuracy of analysis becomes low due to a change in concentration of the reference liquid.

The rotating disk 21 described above is supported by support rollers 31, 31, . . . , which are located at an outer peripheral region of the rotating disk 21. The center region of the rotating disk 21 is supported for rotation around a support shaft (not shown). Also, a timing belt (not shown) is threaded over the outer periphery of the rotating disk 21. The timing belt is rotated forwardly or reversely by a driving motor. The circular non-rotating section 22 is secured to the support shaft and cannot be rotated.

As illustrated in FIG. 3, the dry chemical analysis elements 12, 12, . . . having not been used are introduced into the element cartridge 13 from above. Ordinarily, the plurality of the dry chemical analysis elements 12, 12, . . . , which may be of different types, are superposed one upon another in the element cartridge 13. When the element cartridge 13 is fitted into one of the element loading sections 24, 24, . . . of the sample tray 2, the bottom of the element cartridge 13 is supported by a bottom wall 24a of the element loading section 24. The lowest dry chemical analysis element 12, which is among the plurality of the dry chemical analysis elements 12, 12, . . . superposed one upon another in the element cartridge 13, is located at a height identical with the height of the plane of conveyance of the dry chemical analysis element 12. A left side wall of the element cartridge 13 in FIG. 3 is provided with an opening 13a at a position corresponding to the lowest dry chemical analysis element 12, which is among the plurality of the dry chemical analysis elements 12, 12, . . . superposed one upon another in the element cartridge 13. The size of the opening 13a of the element cartridge 13 is set such that only one dry chemical analysis element 12 is capable of passing through the opening 13*a*. A right side wall of the element cartridge 13 in FIG. 3 is provided with an opening 13*b*, through which the element conveying member 71 is capable of passing.

Also, the bottom surface of the dry chemical analysis element 12 is appended with analysis information (such as information representing the type of the analysis and information representing the production lot number), which has been recorded with the dot recording technique, the bar code recording technique, or the like. Such that the analysis information is capable of being read from below the element cartridge 13, the bottom surface of the element cartridge 13 is provided with a window 13*c*, and the bottom wall 24*a* of the element loading section 24 is provided with a window 24*b*.

Further, reading means 33 for reading the analysis information from the dry chemical analysis element 12 is located under the sample tray 2. The reading means 33 is located such that, when the rotating disk 21 has been rotated by the operation of the sample tray 2 from the position for element takeout illustrated in FIG. 2, and the sample vessel 11 (the sample loading section 23) has thus been moved to the position for sample suction illustrated in FIG. 4, which position for sample suction is located on the movement path of the spotting nozzles 45, 45 (i.e., the element conveyance path R), the reading means 33 is located under the position, to which the element cartridge 13 (the element loading section 24) accommodating the dry chemical analysis element 12 to be used for the analysis of the sample contained in the sample vessel 11 has been moved. Specifically, as illustrated in FIG. 4, the reading means 33 is located at the position, to which the element loading section 24 has been moved in the manner described above, at the phase angle shifted from the element conveyance path R by the phase pitch between the sample loading section 23 and the element loading section 24. In FIG. 2, for clearness, part of the rotating disk 21 is cut away, and the reading means 33 is illustrated at the cut-away area of the rotating disk 21. Also, in FIG. 3, for clearness, the reading means 33 is illustrated under the element loading section 24, which is located on the element conveyance path R.

In cases where the analysis information is recorded with the dot recording technique, the reading means 33 is constituted of a CCD camera. In cases where the analysis information is recorded with the bar code recording technique, the reading means 33 is constituted of a bar code reader. The operation for reading the analysis information from the dry chemical analysis element 12 by use of the reading means 33 is performed before the operation for sucking the sample from the corresponding sample vessel 11 and the operation for conveying the dry chemical analysis element 12 are performed. The analysis information, the production lot information, and the like, are capable of being acquired from a number of six figures or a number of four figures having been obtained from the reading of the information appended to the dry chemical analysis element 12. Also, the front and back surfaces of the dry chemical analysis element 12 and the anterior and posterior directions of the dry chemical analysis element 12 are capable of being recognized in accordance with the recording pattern, or the like. Therefore, an element setting failure is capable of being detected, and a warning is capable of being given. Further, in cases where the type of the analysis is the one requiring the reference liquid and the diluent liquid, and the sample tray 2 comes short of the expendables (nozzle tips 14, 14, . . . , diluent liquid vessels 15, 15, 15, mixing cups 16, 16, . . . , and a reference liquid vessel 17) for the analysis, a warning is capable of being given. Furthermore, in cases where the kind of the sample and the type of the analysis with the dry chemical analysis element 12 do not conform to each other, a warning is capable of being given.

The sample adapter 18 has a cylindrical shape. The sample vessel 11 is inserted into the sample adapter 18 from above. The sample adapter 18 is provided with an identification region (not shown), at which the kind of the sample (processing information), the kind (the size) of the sample vessel 11, and the like, are set. At an initial stage of the analysis, the identification information is read with an identification sensor 30 (shown in FIG. 2), which is located at the outer periphery of the sample tray 2. In this manner, a judgment is made as to whether the sample is to be or is not to be diluted, whether blood filtration is to be or is not to be performed, and the like. Also, an amount of change in liquid level due to the size of the sample vessel 11 is calculated, and processing control is made in accordance with the calculated amount of change in liquid level. In cases where the blood filtration is to be performed, after the sample vessel 11 has been inserted into the sample adapter 18, a holder (not shown) provided with a filter is fitted into the sample vessel 11 via a spacer (not shown).

The spotting section 3 and the transfer mechanism 8 comprise a common support base 61, which is long in the direction normal to the element conveyance path R. The support base 61 is located between the sample tray 2 and the first incubator 4. Also, a sliding frame 62 is located on the plunger 61, such that the sliding frame 62 is capable of moving. A main element retainer 63 and a subsidiary element retainer 64 are fitted to the sliding frame 62. The main element retainer 63 and the subsidiary element retainer 64 are located at positions adjacent to each other and are capable of moving together. As illustrated in FIG. 3, the main element retainer 63 is provided with a spotting opening 63*a*. Also, as illustrated in FIG. 3, the bottom surface of the main element retainer 63, which bottom surface stands facing the support base 61, is provided with a recess 63*b*, through which the dry chemical analysis element 12 is capable of being conveyed along the element conveyance path R. The subsidiary element retainer 64 is constituted in the same manner as that in the main element retainer 63. One end region of the sliding frame 62 is guided by a guide bar 65. The other end region of the sliding frame 62 is provided with a long groove 62*a*. The long groove 62*a* of the sliding frame 62 is engaged with a pin 66. The sliding frame 62 is also provided with a rack gear 62*b*. The rack gear 62*b* of the sliding frame 62 is engaged with a driving gear 67 of a driving motor 68 in order to move the sliding frame 62. The support base 61 is provided with the second incubator 5 described above and the scrapping hole 69 described above.

As illustrated in FIG. 2, when the main element retainer 63 is located at the position corresponding to the position of the spotting section 3, the colorimetric-type dry chemical analysis element 12 having been spotted with the sample is pushed by the element conveying mechanism 7 out of the spotting section 3 and transferred into the first incubator 4. In cases where the spotting onto the electrolyte-type dry chemical analysis element 12 has been performed, the sliding frame 62 is moved, and the electrolyte-type dry chemical analysis element 12, which has been spotted, is slid on the support base 61 in the state, in which the electrolyte-type dry chemical analysis element 12 is being supported by the main element retainer 63. In this manner, the electrolyte-type dry chemical analysis element 12 is transferred into the second incubator 5. At the second incubator 5, the potential difference measurement is performed. At this time, the subsidiary element retainer 64 of the sliding frame 62 moves to the spotting section 3 (i.e., the spotting position). Therefore, with respect to the colorimetric-type dry chemical analysis element 12, which may be conveyed thereafter from the sample tray 2 into the spotting section 3, the sample spotting and the conveyance into the first incubator 4 are capable of being performed. When the analysis at the second incubator 5 is finished, the sliding frame 62 is moved even further in order to transfer the electrolyte-type dry chemical analysis element 12, which has been analyzed, into the scrapping hole 69. The electrolyte-type dry chemical analysis element 12, which has been analyzed, is thus allowed to fall and scrapped.

As illustrated in FIG. 1, the spotting unit 6 comprises the moving frame 42. The moving frame 42 is supported on a horizontal guide rail 41 of a secured frame 40, such that the moving frame 42 is capable of being moved horizontally. The two spotting nozzles 45, 45 are located for vertical movement in the moving frame 42. A vertical guide rail 43 is secured at the center region of the moving frame 42. Also, two nozzle securing bases 44, 44 are supported for sliding movement on opposite sides of the vertical guide rail 43. A top end of the spotting nozzle 45 is secured to the lower area of each of the two nozzle securing bases 44, 44. Also, a shaft-shaped member extending upwardly from the top area of each of the nozzle securing bases 44, 44 is inserted into one of driving force transmitting members 47, 47. Further, a compression spring is located between the nozzle securing base 44 and the driving force transmitting member 47. The compression spring yields the force for fitting the nozzle tip 14. Each of the nozzle securing bases 44, 44 is capable of moving vertically together with the corresponding driving force transmitting member 47. Also, in cases where the nozzle tip 14 is to be fitted onto the bottom end region of the spotting nozzle 45, the driving force transmitting member 47 is capable of compressing the compression spring and moving downwardly with respect to the nozzle securing base 44.

Each of belts 50, 50 is threaded over upper and lower pulleys 49, 49. Each of the driving force transmitting members 47, 47 described above is secured to one of the belts 50, 50. Each of the belts 50, 50 is moved by a motor (not shown), and each of the driving force transmitting members 47, 47 is thereby moved vertically. A balancing weight 51 is secured to an outer region of each of the belts 50, 50 in order to prevent the spotting nozzle 45 from moving down when each of the belts 50, 50 is not driven.

The moving frame 42 is moved horizontally by a belt driving mechanism (not shown). The horizontal movements and the vertical movements of the two nozzle securing bases 44, 44 are controlled such that each of the two nozzle securing bases 44, 44 independently undergoes the vertical movement. The two spotting nozzles 45, 45 move together in the horizontal direction. Also, each of the two spotting nozzles 45, 45 independently undergoes the vertical movement. By way of example, one of the two spotting nozzles 45, 45 is used for the sample, and the other spotting nozzle 45 is used for the diluent liquid and the reference liquid.

Each of the spotting nozzles 45, 45 has a rod-like shape. An axially extending air path is formed within each of the spotting nozzles 45, 45. The pipette-shaped nozzle tip 14 is fitted in a sealed state onto the bottom end region of each of the spotting nozzles 45, 45. An air tube, which is connected to a syringe pump (not shown), or the like, is connected to each of the spotting nozzles 45, 45 in order to supply the suction pressure and the discharging pressure to each of the spotting nozzles 45, 45. The liquid level of the sample, or the like, is capable of being detected in accordance with a change in suction pressure.

The tip scrapping section 9 is located such that the tip scrapping section 9 vertically intersects with the plane of conveyance of the dry chemical analysis element 12. The tip scrapping section 9 comprises an upper member 81 and a lower member 82. The region of the support base 61 described above, which region is located at the position corresponding to the position of the tip scrapping section 9, is provided with an elliptic fall opening 83. The upper member 81 of the tip scrapping section 9 is secured to the top surface of the support base 61. Also, the upper member 81 of the tip scrapping section 9 is provided with an engagement cut-away region 84 at a position exactly above the fall opening 83 of the support base 61. The lower member 82 of the tip scrapping section 9 is formed in a cylindrical shape and is located under the bottom surface of the support base 61 so as to surround the region beneath the fall opening 83 of the support base 61. The lower member 82 of the tip scrapping section 9 guides the nozzle tip 14, which falls from the region within the upper member 81 of the tip scrapping section 9 through the fall opening 83 of the support base 61.

In cases where the nozzle tip 14 having been fitted onto the spotting nozzle 45 is to be removed from the spotting nozzle 75 and scrapped, the spotting nozzle 45, onto which the nozzle tip 14 has been fitted, is moved downwardly into the region within the upper member 81 of the tip scrapping section 9 and is then moved toward the left side in FIG. 3 until the top end region of the nozzle tip 14 engages with the engagement cut-away region 84 of the upper member 81 of the tip scrapping section 9. Thereafter, the spotting nozzle 45 is moved upwardly, and the nozzle tip 14 is thereby removed from the spotting nozzle 45. The nozzle tip 14 having thus been removed from the spotting nozzle 45 is allowed to fall from the region within the upper member 81 of the tip scrapping section 9 through the fall opening 83 of the support base 61 into the lower member 82 of the tip scrapping section 9. The nozzle tip 14 is thus scrapped.

The first incubator 4 for performing the colorimetry comprises an annular rotating member 87, which is located at an outer peripheral region of the first incubator 4. A tapered rotating cylinder 88 is secured to a bottom surface of an inner peripheral region of the rotating member 87. The tapered rotating cylinder 88 is supported for rotation by a bearing 89, which is located at a bottom area of the tapered rotating cylinder 88. A top member 90 is located on the rotating member 87, such that the top member 90 is capable of rotating together with the rotating member 87. The top member 90 has a flat bottom surface. A plurality of recesses (in the case of FIG. 1, 13 recesses) are formed at predetermined intervals in the top circumferential surface of the rotating member 87. In this manner, element compartments 91, 91, . . . are formed as slit-shaped spaces between the rotating member 87 and the top member 90. The height of the bottom surface of each of the element compartments 91, 91, . . . coincides with the height of the plane of conveyance of the dry chemical analysis element 12. The inner hole of the tapered rotating cylinder 88 acts as a scrapping hole 92 for the dry chemical analysis element 12 having been used for the analysis. The dry chemical analysis element 12, which has been accommodated in each of the element compartments 91, 91, . . . and has been used for the analysis, is moved from the element compartment 91 toward the center region of the first incubator 4. The dry chemical analysis element 12 is thus allowed to fall through the scrapping hole 92 and scrapped.

The top member 90 is provided with heating means (not shown). The temperature of the dry chemical analysis element 12, which has been accommodated in each of the element compartments 91, 91, . . . , is kept at a predetermined temperature by the temperature adjustment with the heating means. Also, as illustrated in FIG. 3, the top member 90 is provided with retaining members 93, 93, . . . at the positions corresponding to the element compartments 91, 91, . . . . Each of the retaining members 93, 93, . . . retains the mount of the dry chemical analysis element 12 from above in order to prevent the sample from evaporating. A heat insulating cover 94 is located so as to cover the top surface of the top member 90. Also, the entire area of the first incubator 4 is covered with a light blocking cover 95. Further, an opening 91*a* for photometry is formed at a center area of the bottom surface of each of the element compartments 91, 91, . . . of the rotating member 87, which element compartments 91, 91, . . . accommodate the dry chemical analysis elements 12, 12, . . . . Through the opening 91*a* of each of the element compartments 91, 91, . . . , the measurement of a reflection optical density of each dry chemical analysis element 12 is performed with a photometric head 96, which is located at the position shown in FIG. 2. The first incubator 4 is rotated reciprocally by a belt mechanism (not shown).

The element scrapping mechanism 10 comprises a scrapping bar 101. The scrapping bar 101 is capable of being moved from the outer peripheral side of the first incubator 4 toward the center region of the first incubator 4 and thus entered into each of the element compartments 91, 91, . . . . Also, the scrapping bar 101 is capable of being moved reversely and retracted from the element compartment 91. A tail end region of the scrapping bar 101 is secured to a belt 102, which is moved horizontally by a driving motor 103. The scrapping bar 101 moves in accordance with the movement of the belt 102 in order to push the dry chemical analysis element 12, which has been used for the analysis, out of the element compartment 91 into the scrapping hole 92. A collecting box (not shown) for collecting the dry chemical analysis elements 12, 12, . . . , which have been used for the analyses, is located under the scrapping hole 92.

In the second incubator 5 for the measurement of the ionic activity of the specific ion, the main element retainer 63 of the sliding frame 62 described above acts as a top member, and a single element compartment is formed by the recess at the bottom of the main element retainer 63 and on a top surface of a measuring main body 97. The second incubator 5 is provided with heating means (not shown). The temperature of an ionic activity measurement region of the dry chemical analysis element 12, which has been accommodated in the element compartment, is kept at a predetermined temperature by the temperature adjustment with the heating means. Also, three pairs of potential difference measuring probes 98, 98, . . . for the measurement of the ionic activity are located along the sides of the measuring main body 97. The three pairs of the potential difference measuring probes 98, 98, . . . are capable of being moved and brought into contact with the ion selective electrodes of the dry chemical analysis element 12.

As described above, the blood filtering unit (not shown) for separating blood plasma from blood is located in the vicinity of the sample tray 2. The blood filtering unit operates in the manner described below. Specifically, blood plasma is separated with suction from blood via the holder (not shown), which has been inserted into the sample vessel (blood-collecting tube) 11 supported by the sample tray 2 and is provided with the glass fiber filter fitted to the top end opening of the sample vessel 11. Also, the blood plasma, which has been separated from the blood by the filtration, is retained in a cup region located at the top end of the holder.

How the biochemical analysis apparatus 1 operates will be described hereinbelow. Firstly, before the analyses are performed, preparation for the analyses is made. Specifically, each of the sample vessels 11, 11, . . . accommodating the samples is fitted into one of the sample loading sections 23, 23, . . . of the sample tray 2. Also, each of the element cartridges 13, 13, . . . accommodating the dry chemical analysis elements 12, 12, . . . is fitted into one of the element loading sections 24, 24, . . . . Further, the tip racks 19, 19 accommodating the nozzle tips 14, 14, . . . , are fitted into the tip loading sections 25, 25. Furthermore, the mixing cups 16, 16, . . . are fitted into the cup loading section 27, the diluent liquid vessels 15, 15, 15 are fitted into the diluent liquid loading section 26, and the reference liquid vessel 17 is fitted into the reference liquid loading section 28.

Thereafter, analysis processing is begun. Firstly, in cases where it has been judged that the blood filtration is to be performed with respect to the sample, the whole blood accommodated in the sample vessel 11 is subjected to the filtration with the blood filtering unit, and the blood plasma constituent is obtained.

Thereafter, the rotating disk 21 is rotated, and the element cartridge 13 corresponding to the sample to be analyzed is located at the position for information reading (the position illustrated in FIG. 4), which position corresponds to the position of the reading means 33. In this state, the analysis information, which has been appended to the lowest dry chemical analysis element 12 among the dry chemical analysis elements 12, 12, . . . accommodated in the element cartridge 13, is read from the lowest dry chemical analysis element 12. Thereafter, the rotating disk 21 is rotated, and the element cartridge 13 is located at the position for element takeout (the position illustrated in FIG. 2), which position corresponds to the position of the spotting section 3. The dry chemical analysis element 12, from which the analysis information has thus been read, is then taken out by the element conveying member 71 from the element cartridge 13 and conveyed into the spotting section 3.

In cases where it has been detected from the thus read analysis information that the type of the analysis with the dry chemical analysis element 12 is the colorimetry, the sample tray 2 is rotated, and a nozzle tip 14 accommodated in one of the tip racks 19, 19 is located at the position under one of the spotting nozzles 45, 45. Also, in the manner described above, the spotting nozzle 45 is moved downwardly, and the nozzle tip 14 is fitted onto the end of the spotting nozzle 45. Thereafter, the spotting nozzle 45 is moved upwardly.

Thereafter, the sample tray 2 is rotated in order to locate the sample vessel 11 at the position for sample suction (the position illustrated in FIG. 4). The spotting nozzle 45 is then moved downwardly, and the sample is sucked from the sample vessel 11 into the nozzle tip 14. Thereafter, the spotting nozzle 45 is moved to the position above the spotting section 3, and the sample is spotted from the nozzle tip 14 onto the dry chemical analysis element 12, which has been conveyed to the spotting section 3. At the time of the sample suction, the element cartridge 13 corresponding to the sample vessel 11 is located at the position for information reading, and the analysis information is read simultaneously from a dry chemical analysis element 12, which is now located at the lowest position in the element cartridge 13 and is to be used for the next analysis.

Thereafter, the colorimetric-type dry chemical analysis element 12, which has been spotted with the sample, is inserted from the spotting section 3 into an element compartment 91 of the first incubator 4. After the dry chemical analysis element 12 has been kept at a predetermined temperature for a predetermined time in the element compartment 91, the rotating member 87 of the first incubator 4 is rotated, and the dry chemical analysis element 12 having been inserted into the element compartment 91 of the first incubator 4 is located at the position which stands facing the photometric head 96. In this state, the reflection optical density of the dry chemical analysis element 12 is measured with the photometric head 96. After the measurement of the reflection optical density of the dry chemical analysis element 12 is finished, the dry chemical analysis element 12 having been measured is pushed out from the element compartment 91 toward the center region of the first incubator 4 and into the scrapping hole 92 and is thus scrapped. Also, the results of the measurement are outputted. Further, the nozzle tip 14 having been used is removed from the spotting nozzle 45 in the tip scrapping section 9. In the tip scrapping section 9, the nozzle tip 14 having been removed from the spotting nozzle 45 is allowed to fall and scrapped. At this stage, the processing of the colorimetry is finished.

Also, on the side of the sample tray 2, after the suction and the spotting of the sample described above have been finished, the rotating disk 21 is rotated again, and the element cartridge 13 is located at the position for element takeout, which position corresponds to the position of the spotting section 3. In this state, the dry chemical analysis element 12, from which the analysis information has been read, is taken out from the element cartridge 13 by the element conveying member 71 and conveyed to the spotting section 3 by the element conveying member 71. Thereafter, the sample tray 2 is rotated, and the sample vessel 11 is moved to the position for sample suction. Also, the spotting nozzle 45 is moved downwardly, and the sample is sucked from the sample vessel 11 into the nozzle tip 14. The spotting nozzle 45 is then moved to the spotting section 3, and the sample is spotted onto the dry chemical analysis element 12. At the time of the sample suction, the element cartridge 13 corresponding to the sample vessel 11 is located at the position for information reading, and the analysis information is read simultaneously from a next dry chemical analysis element 12, which is now located at the lowest position in the element cartridge 13 and is to be used for the next analysis. The operations described above are iterated with respect to all of the dry chemical analysis elements 12, 12, . . . accommodated in the element cartridge 13.

In cases where analyses of a sample accommodated in a new sample vessel 11 are to be made, the reading of the analysis information of a first dry chemical analysis element 12 is performed by locating the corresponding element cartridge 13 at the position for information reading (the position illustrated in FIG. 4). Thereafter, the element cartridge 13 is moved to the position for element takeout (the position illustrated in FIG. 2), and the first dry chemical analysis element 12 is taken out from the element cartridge 13 and conveyed to the spotting section 3. Thereafter, in the same manner as that described above, the sample vessel 11 is moved to the position for sample suction (the position illustrated in FIG. 4), and the sample is sucked from the sample vessel 11. Also, at the same time as the suction and the spotting of the sample, the operation for reading the analysis information from a next dry chemical analysis element 12 is performed.

In cases where it has been detected from the read analysis information that the type of the analysis with the dry chemical analysis element 12 is the dilution request type, e.g. in cases where the concentration of the blood is high and it is regarded that an accurate analysis cannot be made, the dry chemical analysis element 12 is conveyed to the position for sample spotting, and a nozzle tip 14 is fitted onto the spotting nozzle 45. The spotting nozzle 45 is then moved downwardly, and the sample is sucked from the sample vessel 11 into the nozzle tip 14. At this time, the operation for reading the analysis information from a next dry chemical analysis element 12 is performed simultaneously. Also, the sucked sample is introduced from the nozzle tip 14 into the mixing cup 16. The nozzle tip 14 having thus been used is then removed from the spotting nozzle 45. Thereafter, a new nozzle tip 14 is fitted onto the spotting nozzle 45, and the diluent liquid is sucked from a diluent liquid vessel 15 into the new nozzle tip 14. The sucked diluent liquid is then discharged from the nozzle tip 14 into the mixing cup 16, into which the sample has been introduced. Also, the nozzle tip 14 is inserted into the mixing cup 16, and the mixture of the sample and the diluent liquid is stirred through repeated suction of the mixture into the nozzle tip 14 and discharging of the mixture from the nozzle tip 14. The sample having thus been diluted with the diluent liquid is then sucked into the nozzle tip 14. The spotting nozzle 45 fitted with the nozzle tip 14 is then moved to the position above the spotting section 3, and the diluted sample is spotted onto the dry chemical analysis element 12. Thereafter, the photometry, the element scrapping, the outputting of results of the measurement, and the tip scrapping are performed in the same manner as that described above, and the processing is finished.

In cases where it has been detected from the read analysis information that the type of the analysis with the dry chemical analysis element 12 is the measurement of the ionic activity, the processing is performed in the manner described below. In the cases of the measurement of the ionic activity, the electrolyte-type dry chemical analysis element 12 is conveyed from the element cartridge 13 into the spotting section 3. Thereafter, firstly, a nozzle tip 14 is fitted onto one of the spotting nozzles 45, 45, and a sample is sucked from the sample vessel 11 into the nozzle tip 14. At this time, the operation for reading the analysis information from a next dry chemical analysis element 12 is performed simultaneously. Thereafter, a nozzle tip 14 is fitted onto the other spotting nozzle 45, and the reference liquid is sucked from the reference liquid vessel 17 into the nozzle tip 14, which has been fitted onto the other spotting nozzle 45. Thereafter, the sample is spotted from the nozzle tip 14, which has been fitted onto the one spotting nozzle 45, into one of the two liquid feeding holes of the dry chemical analysis element 12. Also, the reference liquid is spotted from the nozzle tip 14, which has been fitted onto the other spotting nozzle 45, into the other liquid feeding hole of the dry chemical analysis element 12.

The dry chemical analysis element 12, which has been spotted with the sample and the reference liquid in the manner described above, is transferred from the spotting section 3 into the second incubator 5 in accordance with the movement of the sliding frame 62. When the dry chemical analysis element 12 has thus been inserted into the second incubator 5, the measurement of the ionic activity of the specific ion contained in the sample is performed with the potential difference measuring probes 98, 98, . . . . After the measurement of the ionic activity of the specific ion is finished, the dry chemical analysis element 12 having been measured is transferred into the scrapping hole 69 and scrapped in accordance with the movement of the sliding frame 62. Also, the results of the measurement are outputted. Further, the two nozzle tips 14, 14 having been used are removed from the spotting nozzles 45, 45 and scrapped. At this stage, the processing of the measurement of the ionic activity is finished.

In the embodiment described above, before the dry chemical analysis element 12 is conveyed from the element cartridge 13 to the position for sample spotting in accordance with the rotating operation of the sample tray 2, the analysis information of the dry chemical analysis element 12 is read by the reading means 33, which is located under the sample tray 2. Also, the spotting of the sample corresponding to the type of the analysis is performed in accordance with the thus read analysis information. Further, simultaneously with the suction of the sample from the sample vessel 11 and the spotting of the sample, the operation for reading the analysis information from a dry chemical analysis element 12, which is to be subjected to the spotting next, is performed. Therefore, it is sufficient for the movement for the information reading to be performed only at the first time, and thereafter the movement for the information reading need not be performed. Accordingly, the sequence control is capable of being kept simple, and the time required to make the analyses is capable of being kept short.

Also, the analysis information of the dry chemical analysis element 12 is read before the dry chemical analysis element 12 is taken out from the element cartridge 13. Therefore, a setting failure with respect to the front and back surfaces of the dry chemical analysis element 12 and the anterior and posterior directions of the dry chemical analysis element 12 is capable of being detected in accordance with the information having been read. In such cases, a correcting operation is capable of being performed easily by removing the element cartridge 13 from the sample tray 2 and again accommodating the dry chemical analysis element 12 in a correct state in the element cartridge 13. Also, shortage of expendables to be used for the corresponding analysis, inconformity of the type of the analysis corresponding to the dry chemical analysis element 12 and the kind of the sample with each other, and the like, are capable of being detected in accordance with the information having been read. Therefore, a warning is capable of being given to the operator, and correcting operations are capable of being performed.

FIG. 5 is a schematic plan view showing a major part of a different embodiment of the biochemical analysis apparatus in accordance with the present invention. This embodiment is provided with a sample tray 20 constituted such that the sample loading section 23 for loading the sample vessel 11 and the element loading section 24 for loading the element cartridge 13, in which the dry chemical analysis elements 12, 12, . . . necessary for the analyses of the sample contained in the sample vessel 11 have been accommodated, are located respectively at an inner circumferential section and an outer circumferential section on an identical center line. Also, the reading means 33 for reading the analysis information is located under the sample tray 20 and at the position on the element conveyance path R, to which position the element loading section 24 is rotated. The other features are the same as those of the embodiment described above. In FIG. 5, similar elements are numbered with the same reference numerals with respect to FIG. 4.

In the embodiment of FIG. 5, the position for element takeout and the position for sample suction are set so as to coincide with each other with respect to the rotating movement of the rotating disk 21 of the sample tray 20. Therefore, in cases where a plurality of analyses with the same sample are to be performed successively, particularly in the cases of the colorimetry, the operation for conveying the dry chemical analysis element 12, the operation for sucking the sample, and the operation for spotting the sample are capable of being performed without the rotating movement of the rotating disk 21 being performed. Accordingly, little time loss occurs, and the analyzing efficiency is capable of being enhanced.

In the embodiments described above, the sample tray 2 or the sample tray 20 has the circular shape and undergoes the rotating movement. Alternatively, the sample tray may be constituted as a rack-shaped sample tray undergoing linear movement. In such cases, the reading means 33 is located such that the reading means 33 is capable of reading the analysis information from the dry chemical analysis element 12, which is to be next conveyed to the position for sample spotting, when the sample is located at the position for sample suction.

Further, in the embodiments described above, the reading means 33 is located under the element cartridge 13 (the element loading section 24). Alternatively, the reading means 33 may be located at a position spaced away from the element cartridge 13 (the element loading section 24), from which position the reading means 33 is capable of reading the analysis information of the dry chemical analysis element 12 accommodated in the element cartridge 13.

Figure 8:
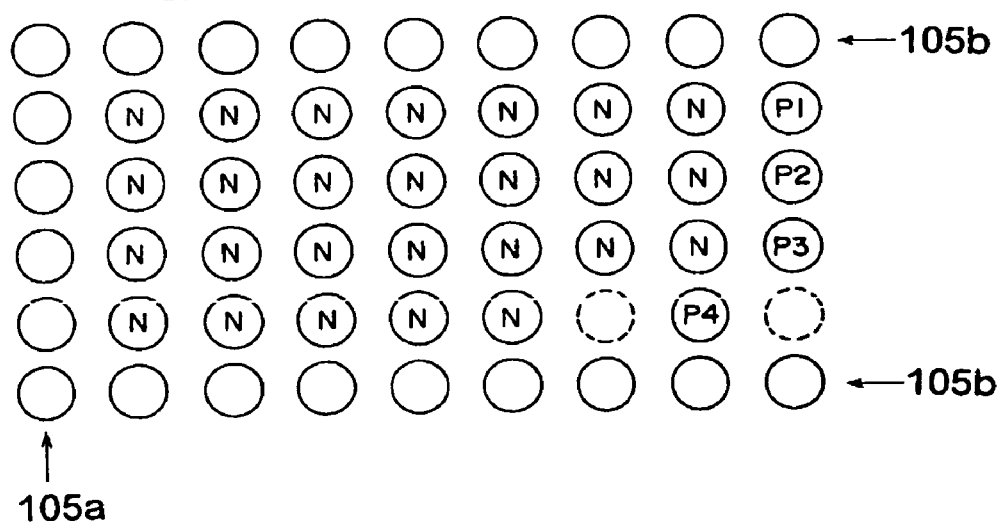
FIG. 8 is an explanatory view showing an example of notation allocation in a dot array pattern.

Embodiments of the dry chemical analysis element for biochemical analysis in accordance with the present invention will be described hereinbelow. FIG. 6A is a plan view showing an embodiment of the dry chemical analysis element for biochemical analysis in accordance with the present invention, which is constituted as a colorimetric-type dry chemical analysis element. FIG. 6B is a bottom view showing the embodiment of the dry chemical analysis element shown in FIG. 6A. FIG. 7A is a plan view showing a different embodiment of the dry chemical analysis element for biochemical analysis in accordance with the present invention, which is constituted as an electrolyte-type dry chemical analysis element. FIG. 7B is a bottom view showing the embodiment of the dry chemical analysis element shown in FIG. 7A. FIG. 8 is an explanatory view showing an example of notation allocation in a dot array pattern.

A colorimetric-type dry chemical analysis element 102 illustrated in FIG. 6A is used for measuring the degree of coloration of the spotted sample. The dry chemical analysis element 102 comprises a rectangular mount section 121, which is made from a plastic material, and an analyzing region 122, which has a reagent layer and is supported within the mount section 121. As illustrated in FIG. 6A, a spotting hole 121a is open at the center area of the front surface of the mount section 121. A front surface of the analyzing region 122 is exposed to the exterior at the spotting hole 121a. The sample is spotted onto the exposed analyzing region 122. Also, as illustrated in FIG. 6B, a photometric hole 121b is open at the center area of the back surface of the mount section 121. A back surface of the analyzing region 122 is exposed to the exterior at the photometric hole 121b. The degree of coloration of the spotted sample is measured with a photometric head of a biochemical analysis apparatus.

Also, as illustrated in FIG. 6B, dot array patterns 105, 105 have been formed respectively at the anterior and posterior areas of the back surface of the mount section 121 of the dry chemical analysis element 102. Each of the dot array patterns 105, 105 is formed at the middle part of the back surface of the mount section 121 with respect to the width direction of the mount section 121 by use of a dot printing technique. Further, a lateral stripe-shaped bar code pattern 106 has been formed with a printing technique and at the area in the vicinity of the photometric hole 121b, which is located at the center area of the back surface of the mount section 121. Furthermore, an analysis type name 107 has been printed on the front surface of the mount section 121 of the dry chemical analysis element 102.

A plurality of kinds of the colorimetric-type dry chemical analysis elements 102, 102, . . . , which correspond to different types of the analyses and have an identical shape, are formed. Each of the colorimetric-type dry chemical analysis elements 102, 102, . . . is provided with the analyzing region 122 containing one of different reagents (coated reagents) The dot array patterns 105, 105 having been encoded as illustrated in FIG. 8 are recorded on the dry chemical analysis element 102 in accordance with the type of the analysis, the production lot information, and the like.

An electrolyte-type dry chemical analysis element 103 illustrated in FIG. 7A is used for measuring the ionic activity of a specific ion contained in the spotted sample. The electrolyte-type dry chemical analysis element 103 comprises a mount section 131 and an analyzing region 132, which is supported within the mount section 131. The mount section 131 has an outside shape approximately identical with the shape of the mount section 121 of the colorimetric-type dry chemical analysis element 102 described above.

As illustrated in FIG. 7A, two liquid receiving holes 131a and 131b have been formed approximately at the center area of the front surface of the mount section 131. The sample is spotted into the liquid receiving hole 131a. The reference liquid, whose ionic activity has been known, is spotted into the liquid receiving hole 131b. Also, as illustrated in FIG. 7B, a pair of ion selective electrodes 132a, 132a have been formed on opposite side areas of the back surface of the mount section 131. Further, a pair of ion selective electrodes 132b, 132b have been formed on opposite side areas of the back surface of the mount section 131. Furthermore, a pair of ion selective electrodes 132c, 132c have been formed on opposite side areas of the back surface of the mount section 131. Potential difference measuring probes (electrode pins) of a biochemical analysis apparatus are electrically connected to the pair of the ion selective electrodes 132a, 132a, the pair of the ion selective electrodes 132b, 132b, and the pair of the ion selective electrodes 132c, 132c of the analyzing region 132. The pair of the ion selective electrodes 132a, 132a are provided with $Cl^-$ ion selective layers. The pair of the ion selective electrodes 132b, 132b are provided with $K^+$ ion selective layers. The pair of the ion selective electrodes 132c, 132c are provided with $Na^+$ ion selective layers.

Also, as illustrated in FIG. 7B, the dot array patterns 105, 105 have been formed respectively at the anterior and posterior areas of the back surface of the mount section 131 of the dry chemical analysis element 103. Each of the dot array patterns 105, 105 is formed at the middle part of the back surface of the mount section 131 with respect to the width direction of the mount section 131 by use of a dot printing technique. Further, though not shown in FIG. 7B, a lateral stripe-shaped bar code pattern has been formed with a printing technique and at the center area of the back surface of the mount section 131.

As illustrated in FIG. 7A, the advance direction of the dry chemical analysis element 103 is indicated on the front surface of the mount section 131 of the dry chemical analysis element 103, such that the user is capable of recognizing the advance direction of the dry chemical analysis element 103. Specifically, as for the electrolyte-type dry chemical analysis element 103, it is necessary that the positions of the potential difference measuring probes and the position of the dry chemical analysis element 103 are matched with each other, and therefore the advance direction of the dry chemical analysis element 103 is defined.

The analyzing region 132 of the electrolyte-type dry chemical analysis element 103 is provided with a porous bridge. The porous bridge is located so as to communicate the pair of the ion selective electrodes 132a, 132a, at which potentials corresponding to the ionic activities of the specific ion occur, with each other, so as to communicate the pair of the ion selective electrodes 132b, 132b, at which potentials corresponding to the ionic activities of the specific ion occur, with each other, and so as to communicate the pair of the ion selective electrodes 132c, 132c, at which potentials corresponding to the ionic activities of the specific ion occur, with each other. When the sample and the reference liquid are spotted respectively to the liquid receiving holes 131a and 131b, the interfaces of the sample and the reference liquid come into contact with each other by the effect of the porous bridge, and electrical conduction occurs between the sample and the reference liquid. As a result, a potential difference occurs between each pair of the ion selective electrodes in accordance with the difference between the ionic activities of the ion in the sample and the reference liquid. The potential difference is measured, and the ionic activity of the specific ion contained in the sample is calculated in accordance with the measured potential difference and by use of a calibration curve having been determined previously (in accordance with the principle of the Nernst equation).

The bar code pattern 106 has heretofore been printed at the position described above. The dot array patterns 105, 105 are formed at the positions other than the position of the bar code pattern 106 and the position for the reading with the bar code reader (the side edge area). Specifically, the dot array patterns 105, 105 are formed on the side more anterior than the bar code pattern 106 and on the side more posterior than the bar code pattern 106 and at the center area with respect to the width direction of the dry chemical analysis element. With the conventional biochemical analysis apparatus, the side edge area of the dry chemical analysis element 102 or the dry chemical analysis element 103 being conveyed is scanned with the bar code reader of the biochemical analysis apparatus, the bar code pattern 106 is thus read, the type of the analysis is discriminated in accordance with the thus read bar code pattern 106, and the spotting, the conveyance, the keeping at the predetermined temperature, and the measurement are controlled in accordance with the discriminated type of the analysis. The dot array patterns 105, 105 are located so as not to obstruct the operations of the biochemical analysis apparatus.

The dot array pattern 105 may be formed at only either one of the anterior and posterior areas of the back surface of the mount section 121 of the dry chemical analysis element 102 or the mount section 131 of the dry chemical analysis element 103.

FIG. 8 is an explanatory view showing an example of notation allocation in the dot array pattern 105. The dot array pattern 105 is a matrix comprising six rows and nine columns. The first left-hand column represents a start code 105a. Dot setting positions of the matrix are represented by reference dots 105b, 105b located along the first row and the sixth row. The dots appended with a sign N represents a slide type number, a slide sample kind number, a production lot number, and other inherent numbers concerning the production. P1 to P4 are parity dots. The two dots indicated by the broken lines are spaces with no notation.

In cases where each piece of information is expressed with the binary notation, each of the dots described above is set in the manner described below. Specifically, in cases where the subject bit is at a "1" level, dot notation is effected. Also, in cases where the subject bit is at a "0" level, dot notation is not effected. Also, the parity dots P1 to P4 are utilized for the parity check in the manner described below. Specifically, in cases where the dot notation of each row is of an odd number, dot notation is effected. Also, in cases where the dot notation of each row is of an even number, dot notation is not effected. Further, the spaces with no notation are utilized for the discrimination of the advance direction of the dry chemical analysis element 102 or the dry chemical analysis element 103.

The slide type number and the slide sample kind number described above represent the analysis type information. The production lot number and other inherent numbers concerning the production represent the production lot information. Each of these pieces of information is encoded and expressed with the dot array pattern. The dot array pattern 105 maybe recorded by use of a plurality of colors, and the amount of information may thereby be kept large. Also, serviceable life information may also be recorded.

The direction of the start code of the dot array pattern 105 of the colorimetric-type dry chemical analysis element 102 and the direction of the start code of the dot array pattern 105 of the electrolyte-type dry chemical analysis element 103 are set to be identical with each other.

The biochemical analysis apparatus for making the analysis of the constituent of the sample by use of the dry chemical analysis element 102 and the dry chemical analysis element 103 comprises a sample tray for loading the sample, the dry chemical analysis element 102, the dry chemical analysis element 103, the reference liquid, and the like. The biochemical analysis apparatus also comprises information reading means constituted of a CCD camera for reading the dot array patterns 105, 105 of the dry chemical analysis element 102 and the dot array patterns 105, 105 of the dry chemical analysis element 103. The biochemical analysis apparatus further comprises a spotting unit for sucking the sample into a spotting nozzle and spotting the sample onto the dry chemical analysis element 102, and for sucking the sample and the reference liquid into spotting nozzles and spotting the sample and the reference liquid onto the dry chemical analysis element 103. The biochemical analysis apparatus still further comprises incubators for keeping the spotted dry chemical analysis element 102 and the spotted dry chemical analysis element 103 at predetermined temperatures. The biochemical analysis apparatus also comprises concentration measuring means provided with a photometric head for colorimetry and potential difference measuring means provided with potential difference measuring probes for ionic activity measurement. The biochemical analysis apparatus further comprises a control unit for controlling the operations of the respective sections of the biochemical analysis apparatus and calculating the substance concentration and the ionic activity from the measured values. The control unit stores a plurality of pieces of analysis management information having been read from a magnetic card. Also, the control unit has the functions for making a judgment as to the matching of the information, which has been read from the dot array patterns 105, 105 of the dry chemical analysis element 102 and the dry chemical analysis element 103, and the analysis management information with each other. The plurality of pieces of analysis management information are thus capable of being stored, and the dry chemical analysis elements 102, 102, . . . and the dry chemical analysis elements 103, 103, . . . , which are of different production lots, are capable of being loaded in a mixed form and utilized for the analyses.

In cases where a sample analysis is to be made with the biochemical analysis apparatus described above, the operator sets the dry chemical analysis element 102 or the dry chemical analysis element 103, which is of the kind corresponding to the analysis of the sample, on the sample tray of the biochemical analysis apparatus directly or in the form accommodated in an element cartridge. A bottom surface of the element loading section is provided with a window, which allows the reading of the dot array patterns 105, 105 from below. Also, the information reading means constituted of the CCD camera is located under the window. The colorimetric-type dry chemical analysis elements 102, 102, . . . and the electrolyte-type dry chemical analysis elements 103, 103, . . . described above are set in the mixed form on the sample tray of the biochemical analysis apparatus.

The operation for reading the dot array patterns 105, 105 from the dry chemical analysis element 102 or the dry chemical analysis element 103 is performed before the conveyance of the dry chemical analysis element 102 or the dry chemical analysis element 103 is started. The spotting operation, the operation for keeping the dry chemical analysis element at the predetermined temperature, and the like, are controlled in accordance with the type of the analysis and the sample kind information, which have been obtained from the information reading. Also, the production lot and the analysis management information are matched with each other in accordance with the production lot information, and the measurement data processing is performed accurately in accordance with the analysis management information corresponding to the production lot. Further, the front and back surfaces of the dry chemical analysis element and the anterior and posterior direction of the dry chemical analysis element are capable of being detected. Therefore, a setting failure of the dry chemical analysis element 102 or the dry chemical analysis element 103 is capable of being detected, and a warning is capable of being given. Furthermore, in cases where the type of the analysis is the one requiring the reference liquid and the diluent liquid, and the sample tray comes short of the expendables for the analysis, a warning is capable of being given. Also, in cases where the kind of the sample and the type of the analysis with the dry chemical analysis element 102 or the dry chemical analysis element 103 do not conform to each other, a warning is capable of being given.

With the aforesaid embodiment of the dry chemical analysis element for biochemical analysis in accordance with the present invention, the production lot of the dry chemical analysis element 102 or the dry chemical analysis element 103 used for the analysis and the analysis management information are capable of being matched with each other. Therefore, the biochemical analysis is capable of being performed accurately, and the time required to make the analysis is capable of being kept short.

Also, the information of the dry chemical analysis element 102 or the dry chemical analysis element 103 is capable of being read before the conveyance of the dry chemical analysis element 102 or the dry chemical analysis element 103 is started. Therefore, a setting failure with respect to the front and back surfaces of the dry chemical analysis element and the anterior and posterior direction of the dry chemical analysis element is capable of being detected in accordance with the information having been read. In cases where the setting failure is detected, the setting of the dry chemical analysis element 102 or the dry chemical analysis element 103 is capable of being performed again, and the correcting operation is thus capable of being performed easily.

What is claimed is:

1. A dry chemical analysis element for biochemical analysis, comprising: i) a mount section, and ii) an analyzing region, which is to be spotted with a sample, the analyzing region being supported on the mount section, wherein analysis type information, production lot information, and advance direction information have been recorded on a surface of the mount section and with a dot recording technique for recording information by a dot array pattern, wherein the advance direction information is recorded by the absence of notation at a dot located at a specific site in the dot array pattern.

2. A dry chemical analysis element for biochemical analysis as defined in claim 1 wherein the dot array pattern is recorded at a position other than positions which overlap upon a bar code recording region having already been formed on the mount section, and both the dot array pattern and a bar code are capable of being recorded on the dry chemical analysis element.

3. A dry chemical analysis element for biochemical analysis as defined in claim 1 wherein the dot array pattern is recorded by use of a plurality of colors.

* * * * *